US011160527B2

(12) United States Patent
Osugi

(10) Patent No.: US 11,160,527 B2
(45) Date of Patent: Nov. 2, 2021

(54) RADIATION IMAGING SYSTEM

(71) Applicant: CANON KABUSHIKI KAISHA, Tokyo (JP)

(72) Inventor: Takuya Osugi, Machida (JP)

(73) Assignee: Canon Kabushiki Kaisha, Tokyo (JP)

(*) Notice: Subject to any disclaimer, the term of this patent is extended or adjusted under 35 U.S.C. 154(b) by 497 days.

(21) Appl. No.: 16/103,292

(22) Filed: Aug. 14, 2018

(65) Prior Publication Data
US 2019/0059845 A1 Feb. 28, 2019

(30) Foreign Application Priority Data
Aug. 22, 2017 (JP) .............................. JP2017-159759

(51) Int. Cl.
*A61B 6/00* (2006.01)
*G16H 30/20* (2018.01)

(52) U.S. Cl.
CPC ............ *A61B 6/566* (2013.01); *A61B 6/5294* (2013.01); *A61B 6/548* (2013.01); *G16H 30/20* (2018.01)

(58) Field of Classification Search
CPC ....... A61B 6/566; A61B 6/5294; A61B 6/548; G16H 30/20
See application file for complete search history.

(56) References Cited

U.S. PATENT DOCUMENTS

| | | | | |
|---|---|---|---|---|
| 6,431,751 B1 * | 8/2002 | Everett | ................ | A61B 6/4233 378/193 |
| 7,324,679 B2 * | 1/2008 | Moriyama | ............. | G03B 42/00 382/132 |
| 7,751,529 B2 * | 7/2010 | Ohara | ...................... | A61B 6/56 378/116 |
| 7,772,560 B2 * | 8/2010 | Ohta | ........................ | A61B 6/56 250/370.09 |
| 8,203,446 B2 * | 6/2012 | Tsubota | ................ | H04W 48/02 340/539.1 |
| 8,229,202 B2 * | 7/2012 | Kito | ........................ | A61B 6/542 382/132 |
| 8,259,904 B2 * | 9/2012 | Tsubota | ................. | G03B 42/04 378/116 |
| 8,295,439 B2 * | 10/2012 | Yonekawa | ........... | A61B 6/4216 378/116 |
| 8,330,597 B2 * | 12/2012 | Nishino | ............... | A61B 6/4283 340/540 |

(Continued)

FOREIGN PATENT DOCUMENTS

JP 2011-177348 A 9/2011

*Primary Examiner* — David P Porta
*Assistant Examiner* — Djura Malevic
(74) *Attorney, Agent, or Firm* — Canon U.S.A., Inc. IP Division

(57) ABSTRACT

A radiation imaging system includes a plurality of radiation imaging apparatuses each of which includes a radiation detecting unit that performs an imaging operation for capturing a radiation image based on radiation radiated from a radiation generating apparatus, a control apparatus that communicates with the plurality of radiation imaging apparatuses, a calculation unit that calculates information indicating whether a part or all of pixels of the radiation image are saturated, and an image acquiring unit that acquires a radiation image from a radiation imaging apparatus selected from among the plurality of radiation imaging apparatuses based on the information.

16 Claims, 13 Drawing Sheets

(56) References Cited

U.S. PATENT DOCUMENTS

| | | | | |
|---|---|---|---|---|
| 8,358,740 B2* | 1/2013 | Nakatsugawa | A61B 6/487 | 378/116 |
| 8,546,777 B2* | 10/2013 | Utsunomiya | A61B 6/4283 | 250/580 |
| 8,552,392 B2* | 10/2013 | Kito | G03B 42/04 | 250/370.09 |
| 8,576,087 B2* | 11/2013 | Kamiya | A61B 6/4283 | 340/687 |
| 8,704,188 B2* | 4/2014 | Kitano | A61B 6/4494 | 250/370.09 |
| 8,705,700 B2* | 4/2014 | Eguchi | A61B 6/4494 | 378/116 |
| 8,727,619 B2* | 5/2014 | Yamamichi | G01T 1/17 | 378/207 |
| 8,731,141 B2* | 5/2014 | Kuwabara | A61B 6/4233 | 378/116 |
| 8,823,835 B2* | 9/2014 | Machida | G06T 5/40 | 348/239 |
| 8,855,691 B2* | 10/2014 | Kamiya | A61B 6/566 | 455/500 |
| 9,001,972 B2* | 4/2015 | Takahashi | H05G 1/30 | 378/98 |
| 9,168,011 B2* | 10/2015 | Nenoki | A61B 6/545 | |
| 9,186,118 B2* | 11/2015 | Yonekawa | A61B 6/566 | |
| 9,204,855 B2* | 12/2015 | Tsubota | H04W 76/10 | |
| 9,216,006 B2* | 12/2015 | Kuwabara | A61B 6/4233 | |
| 9,247,163 B2* | 1/2016 | Sato | G01T 1/17 | |
| 9,289,182 B2* | 3/2016 | Yonekawa | A61B 6/4494 | |
| 9,299,141 B2* | 3/2016 | Takahashi | G06T 5/002 | |
| 9,453,923 B2* | 9/2016 | Eguchi | A61B 6/4494 | |
| 9,538,978 B2* | 1/2017 | Makino | G16H 40/63 | |
| 9,880,111 B2* | 1/2018 | Oda | A61B 6/467 | |
| 10,039,509 B2* | 8/2018 | Okusu | A61B 6/4208 | |
| 10,045,751 B2* | 8/2018 | Okusu | A61B 6/46 | |
| 10,105,114 B2* | 10/2018 | Shimizukawa | A61B 6/4283 | |
| 10,368,823 B2* | 8/2019 | Uchiyama | A61B 6/4266 | |
| 10,379,232 B2* | 8/2019 | Nakano | A61B 6/4233 | |
| 10,485,505 B2* | 11/2019 | Yamada | A61B 6/5241 | |
| 10,682,105 B2* | 6/2020 | Shimizukawa | A61B 6/4411 | |
| 2004/0071263 A1* | 4/2004 | Motoki | G16H 40/63 | 378/98 |
| 2005/0043620 A1* | 2/2005 | Fallows | A61B 8/565 | 600/437 |
| 2005/0238138 A1* | 10/2005 | Imai | A61B 6/488 | 378/95 |
| 2006/0016998 A1* | 1/2006 | Ohara | A61B 6/4494 | 250/370.11 |
| 2008/0049901 A1* | 2/2008 | Tamakoshi | A61B 6/566 | 378/98.2 |
| 2008/0317214 A1* | 12/2008 | Maack | A61B 6/4494 | 378/162 |
| 2009/0022276 A1* | 1/2009 | Ohara | A61B 6/4233 | 378/101 |
| 2009/0032745 A1* | 2/2009 | Kito | A61B 6/00 | 250/582 |
| 2009/0189761 A1* | 7/2009 | Nishino | A61B 6/4283 | 340/540 |
| 2009/0196398 A1* | 8/2009 | Ohara | A61B 6/4494 | 378/98.5 |
| 2010/0054417 A1* | 3/2010 | Nishino | G03B 42/04 | 378/98.8 |
| 2011/0026676 A1* | 2/2011 | Takekoshi | A61B 6/58 | 378/98.2 |
| 2011/0051896 A1* | 3/2011 | Abe | A61B 6/00 | 378/98.8 |
| 2011/0211672 A1* | 9/2011 | Kuwabara | A61B 6/00 | 378/62 |
| 2011/0317809 A1* | 12/2011 | Eguchi | A61B 6/566 | 378/62 |
| 2012/0002083 A1* | 1/2012 | Machida | G06T 5/009 | 348/239 |
| 2012/0207278 A1* | 8/2012 | Yonekawa | A61B 6/4233 | 378/98.5 |
| 2012/0286167 A1* | 11/2012 | Eguchi | A61B 6/4494 | 250/393 |
| 2012/0328078 A1* | 12/2012 | Kuwabara | H04N 5/32 | 378/62 |
| 2013/0038738 A1* | 2/2013 | Ando | A61B 6/587 | 348/162 |
| 2013/0068955 A1* | 3/2013 | Matsuura | G01T 1/247 | 250/370.09 |
| 2014/0219536 A1* | 8/2014 | Takahashi | G06T 5/10 | 382/132 |
| 2014/0239186 A1* | 8/2014 | Sato | H04N 5/32 | 250/393 |
| 2014/0254760 A1* | 9/2014 | Hiroike | A61B 6/4233 | 378/62 |
| 2014/0284491 A1* | 9/2014 | Sato | G01T 1/247 | 250/393 |
| 2015/0071414 A1* | 3/2015 | Oda | A61B 6/4283 | 378/207 |
| 2016/0025865 A1* | 1/2016 | Wayama | A61B 6/542 | 250/370.07 |
| 2018/0182102 A1* | 6/2018 | Jerebko | G06T 7/0014 | |

* cited by examiner

RADIATION IMAGING SYSTEM

BACKGROUND

Field

The present disclosure relates to a radiation imaging system that uses a radiation imaging apparatus that detects radiation.

Description of the Related Art

Recently, digitalization of radiation imaging systems including radiation imaging apparatuses that generate a digital radiation image based on radiation that is radiated has been widely used. By the digitalization of the radiation imaging systems, it is possible to check an image immediately after radiation imaging, so that workflow is significantly improved in comparison with a case where imaging is performed by a conventional method using a film or a CR apparatus, thus making it possible to perform radiation imaging in an early cycle.

These radiation imaging systems include a radiation imaging apparatus and an imaging control apparatus that receives and uses a radiation image from the radiation imaging apparatus, and the radiation imaging acquired by the radiation imaging apparatus is transmitted as an image to an external imaging control apparatus. In a case where a user selects one radiation imaging apparatus from among a plurality of radiation imaging apparatuses to perform radiation imaging, the imaging control apparatus needs to be notified which radiation imaging apparatus an image is to be acquired from. The imaging control apparatus communicates with the radiation imaging apparatus targeted for notification to acquire the image. When the user uses a radiation imaging apparatus different from the radiation imaging apparatus targeted for notification, the imaging control apparatus can experience difficulty acquiring a radiation image.

In a radiation imaging system described in. Japanese Patent Laid-Open No. 2011-177348, a plurality of radiation imaging apparatuses are enabled to perform imaging, and an imaging control apparatus acquires radiation images from all the plurality of radiation imaging apparatuses and selects and uses a significant radiation image.

However, in the radiation imaging system described in Japanese Patent Laid-Open No. 2011-177348, there is a possibility that the imaging control apparatus selects an image from an incorrect radiation imaging apparatus.

SUMMARY

The present disclosure is provided in view of the above, and improves accuracy in selection of a significant radiation image from a plurality of radiation imaging apparatuses that perform imaging. A radiation imaging system of the present disclosure includes a plurality of radiation imaging apparatuses each of which includes a radiation detecting unit that performs an imaging operation for capturing a radiation image based on radiation radiated from a radiation generating apparatus, a control apparatus that communicates with the plurality of radiation imaging apparatuses, a calculation unit that calculates information indicating whether a part or all of pixels of the radiation image are saturated, and an image acquiring unit that acquires a radiation image from a radiation imaging apparatus selected from among the plurality of radiation imaging apparatuses based on the information.

Further features will become apparent from the following description of exemplary embodiments with reference to the attached drawings.

DESCRIPTION OF THE EMBODIMENTS

Hereinafter, exemplary embodiments of the present disclosure will be described with reference to attached drawings. Note that, the following embodiments are not limiting and all combinations of features described in the embodiments are not always necessary to achieve the functions of the embodiments. Radiation as described in the embodiments can include beams each having a similar degree or more of energy, such as an X-ray, a particle beam, and a cosmic ray, in addition to an alpha ray, a beta ray, and a gamma ray that serve as a beam formed by particles (including photons) emitted by radioactive decay.

First Embodiment

Figure 1:
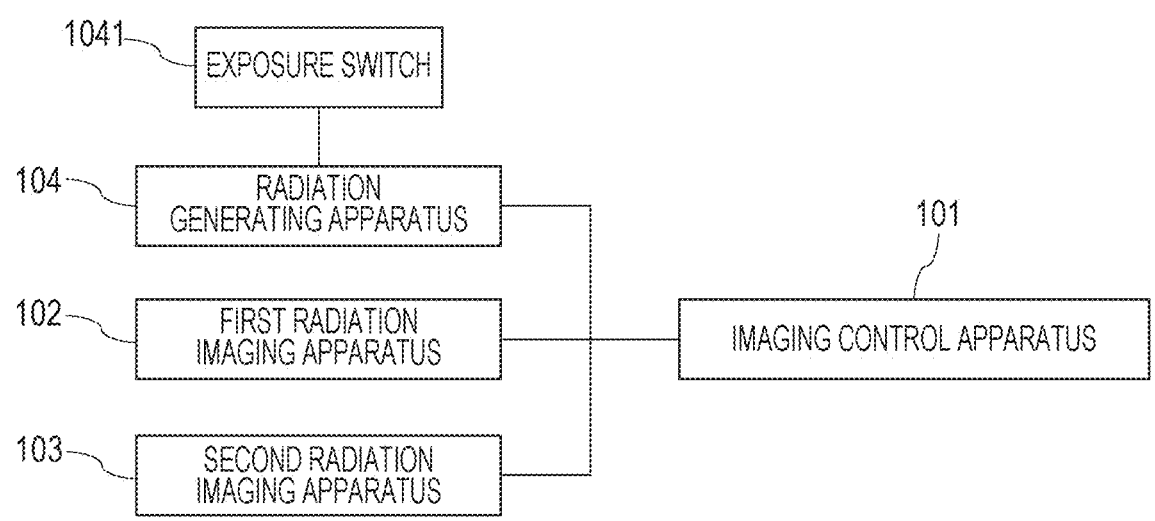
FIG. 1 is a block diagram illustrating an example of a functional configuration of a radiation imaging system of a first embodiment.

FIG. 1 is a diagram illustrating an example of a functional configuration of a radiation imaging system in a first embodiment. The radiation imaging system of the present embodiment includes a radiation generating apparatus 104, a plurality of radiation imaging apparatuses each of which generates an image based on the radiation radiated from the radiation generating apparatus 104, and a control apparatus that communicates with the plurality of radiation imaging apparatuses. In the present embodiment, an imaging control apparatus 101 is provided as an example of the control apparatus, and a first radiation imaging apparatus 102 and a second radiation imaging apparatus 103 are provided as an example of the plurality of radiation imaging apparatuses. The radiation generating apparatus 104 transmits an irradiation start notice to all available radiation imaging apparatuses in response to "on" of an exposure switch 1041. Each of the radiation imaging apparatuses that receive the irradiation start notice starts an imaging operation (accumulation of an electric charge) and transmits an irradiation permission notice to the radiation generating apparatus 104. The radiation generating apparatus 104 receives irradiation permission notices from all available radiation imaging apparatuses (the first radiation imaging apparatus 102 and the second radiation imaging apparatus 103 in the present embodiment) and performs irradiation with radiation. Such an operation provides for synchronization of the radiation generating apparatus 104 and the radiation imaging apparatuses 102 and 103.

The imaging control apparatus 101 communicates with the first radiation imaging apparatus 102 and the second radiation imaging apparatus 103 that are connected thereto and controls radiation imaging. The imaging control apparatus 101 also communicates with the radiation generating apparatus 104 and acquires information when radiation is radiated from the radiation generating apparatus 104. Note that, the number of radiation imaging apparatuses is not limited to two and can be three or more. In the present embodiment, a configuration in which two radiation imaging apparatuses are included will be described as an example.

Figure 2:
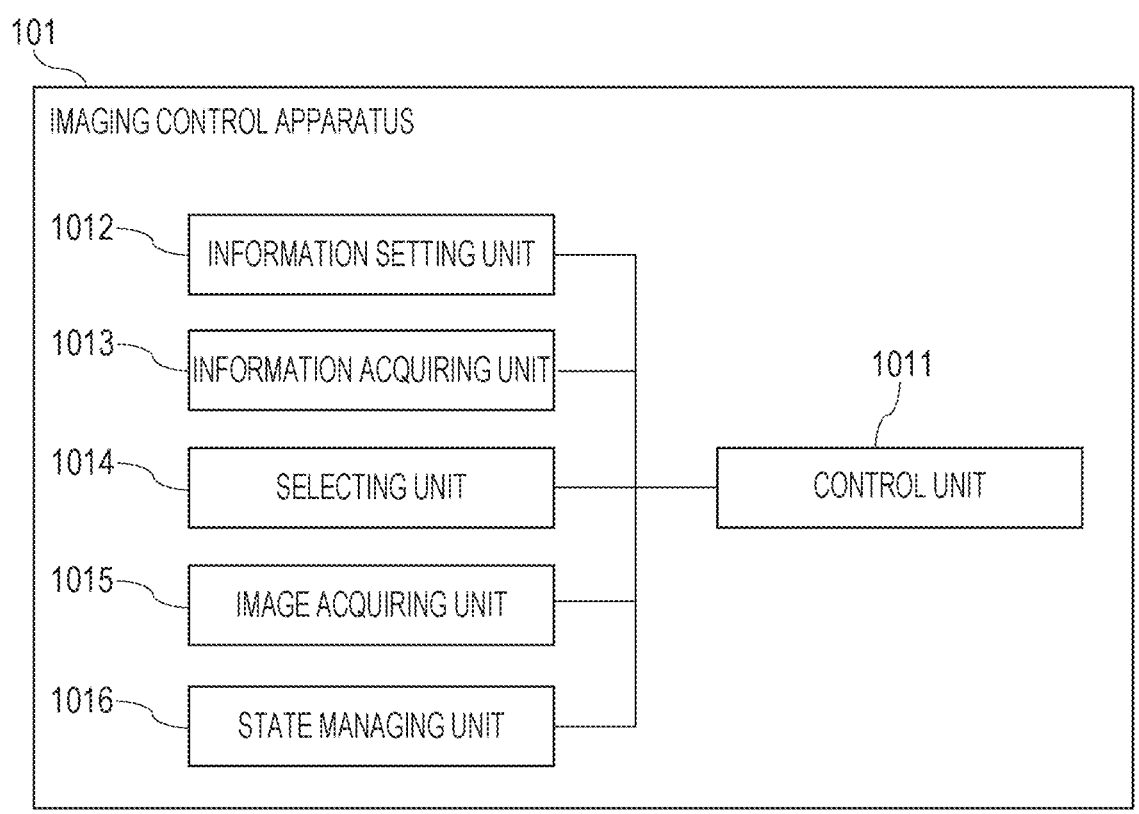
FIG. 2 is a block diagram illustrating an internal structure of an imaging control apparatus of the first embodiment.

FIG. 2 illustrates an internal structure of the imaging control apparatus 101. As illustrated in FIG. 2, in the imaging control apparatus 101, a control unit 1011 controls an information setting unit 1012, an information acquiring unit 1013, a selecting unit 1014, an image acquiring unit 1015, and a state managing unit 1016. The information setting unit 1012 sets pixel characteristic information and/or irradiation information, which is acquired from the radiation generating apparatus 104, to the plurality of radiation imaging apparatuses (the first radiation imaging apparatus 102 and the second radiation imaging apparatus 103). The pixel characteristic information and the irradiation information will be described in detail later.

The information acquiring unit 1013 acquires information based on a radiation image from each of the plurality of radiation imaging apparatuses and acquires, from the radiation generating apparatus 104, the irradiation information when radiation is radiated. The selecting unit 1014 selects one radiation imaging apparatus from among the plurality of radiation imaging apparatuses based on the information acquired by the information acquiring unit 1013. The image acquiring unit 1015 acquires a radiation image from the one radiation imaging apparatus that is selected by the selecting unit 1014. The state managing unit 1016 communicates with the first radiation imaging apparatus 102 or the second radiation imaging apparatus 103 to manage and control a state thereof.

Figure 3:
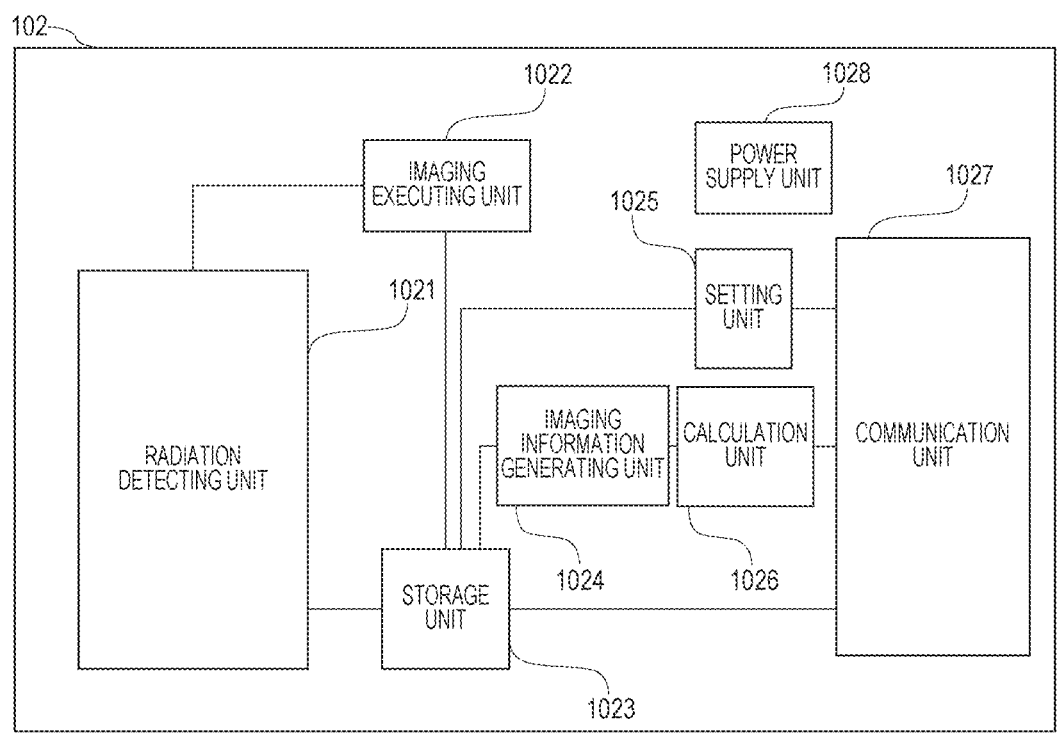
FIG. 3 is a block diagram illustrating an internal structure of a radiation imaging apparatus of the first embodiment.

FIG. 3 illustrates an internal structure of the first radiation imaging apparatus 102. As illustrated in FIG. 3, the radiation imaging apparatus 102 includes a radiation detecting unit 1021, an imaging executing unit 1022, a storage unit 1023, an imaging information generating unit 1024, a setting unit 1025, a calculation unit 1026, a communication unit 1027, and a power supply unit 1028. The radiation detecting unit 1021 includes a function of detecting radiation radiated from the radiation generating apparatus 104, converting the radiation into an electric charge, and accumulating the electric charge. The storage unit 1023 stores, for example, a radiation image generated by an imaging operation of the imaging executing unit 1022, the pixel characteristic information and the irradiation information received from the imaging control apparatus 101.

The storage unit 1023 is a device that reads and writes, and an example thereof includes a volatile memory such as a RAM. However, the storage unit 1023 is not limited thereto and can be a non-volatile memory such as a flash memory. The imaging information generating unit 1024 includes a function of generating, based on the radiation image stored in the storage unit 1023, imaging information whose data size is smaller than that of the radiation image. The setting unit 1025 includes a function of setting, to the storage unit 1023, an image determination condition that is received from the imaging control apparatus 101 via the communication unit 1027 and the irradiation information that is received from the imaging control apparatus 101 or the radiation generating apparatus 104. While the pixel characteristic information received from the imaging control apparatus 101 is set in the storage unit 1023 in the present embodiment, it can be configured such that the pixel characteristic information is stored in the storage unit 1023 of each of the radiation imaging apparatuses in advance. While the irradiation time received from the radiation generating apparatus 104 is set in the storage unit 1023 in the present embodiment, it can be configured such that the radiation imaging apparatus autonomously calculates an irradiation time when an imaging operation is performed and sets the irradiation time in the storage unit 1023.

The calculation unit 1026 includes a function of generating pixel saturation information based on the radiation image generated by the imaging operation, or the imaging information generated by the imaging information generating unit 1024, and the pixel characteristic information stored by the setting unit 1025. Here, the pixel saturation information is information indicating whether a part or all of pixels of the radiation image are saturated. The communication unit 1027 includes a function of transmitting the radiation image stored in the storage unit 1023, the imaging information generated by the imaging information generating unit 1024, or the pixel saturation information to the imaging control apparatus 101 at any timing. The communication unit 1027 also includes a function of notifying the setting unit 1025 of the pixel characteristic information or time information that is notified from the imaging control apparatus 101.

The imaging executing unit 1022 includes a function of performing an imaging operation by controlling the radiation detecting unit 1021 and causing the storage unit 1023 to store a radiation image that is generated. The power supply unit 1028 includes a circuit that supplies power to each of the units of the first radiation imaging apparatus 102. The second radiation imaging apparatus 103 also has a similar functional configuration.

Figure 4:
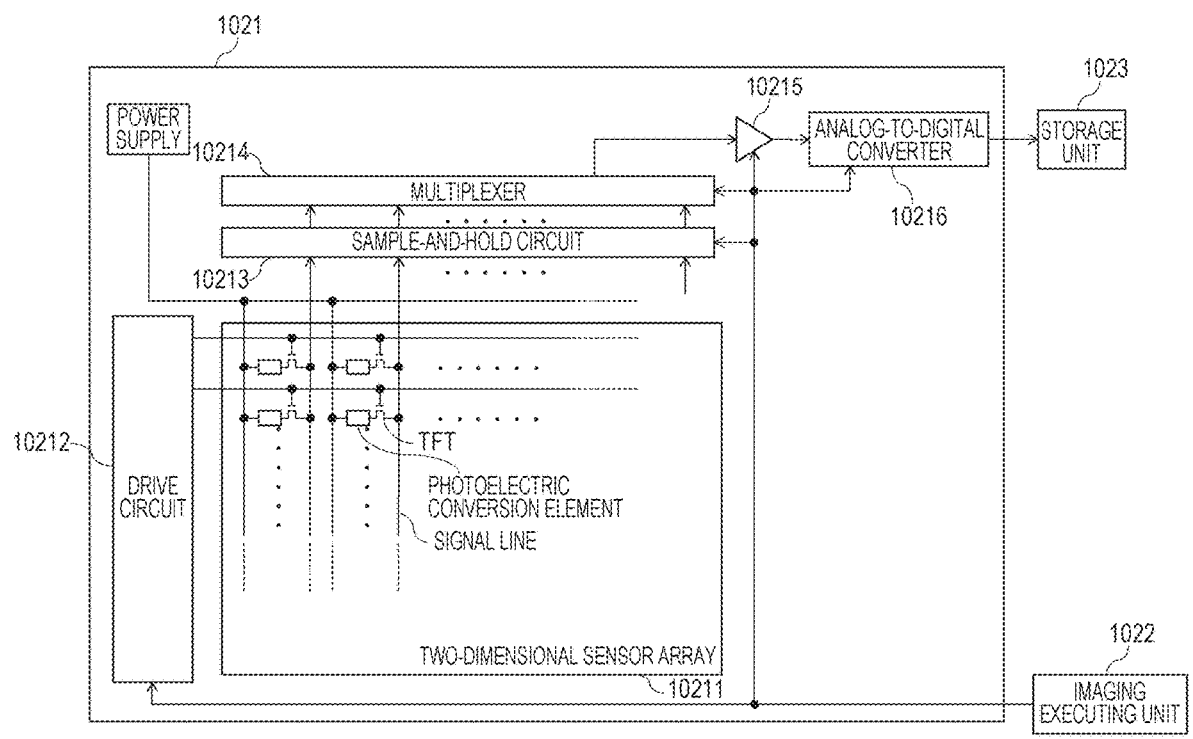
FIG. 4 is a block diagram illustrating an internal structure of a radiation detecting unit of the first embodiment.

FIG. 4 illustrates an example of the radiation detecting unit 1021. The radiation detecting unit 1021 includes a two-dimensional sensor array 10211, a drive circuit 10212, a sample-and-hold circuit 10213, a multiplexer 10214, an amplifier 10215, and an analog-to-digital converter 10216. All pixels one a row of the two-dimensional sensor array 10211 are simultaneously addressed by the drive circuit 10212, and an electric charge accumulation operation by which electric charges of the pixels in the row are held in the sample-and-hold circuit 10213 is performed. Then the stored electric charges output from the pixels are sequentially read through the multiplexer 10214 and amplified by the amplifier 10215, and then converted into digital values by the analog-to-digital converter 10216. Every time scanning of each row is finished, the drive circuit 10212 sequentially drives and scans the next row of the two-dimensional sensor array 10211, and finally, an image generation operation by which electric charges output from all the pixels are converted into digital values is performed.

At this time, scanning is performed while a voltage applied to each of column signal lines is fixed to a specific value, and the acquired electric charges are discarded, so that dark electric charges are discharged, and then an imaging preparation operation that is scanning through which the two-dimensional sensor array 10211 is initialized is performed. The imaging preparation operation, the electric charge accumulation operation, and the image generation operation of the radiation detecting unit 1021 are controlled by the imaging executing unit 1022. An image converted into a digital value is subjected to offset correction in which an offset image acquired from only a dark electric charge component without emitting the radiation is subtracted from the radiation image, thus making it possible to obtain a radiation image from which an unnecessary dark electric charge component is removed.

Figure 5:
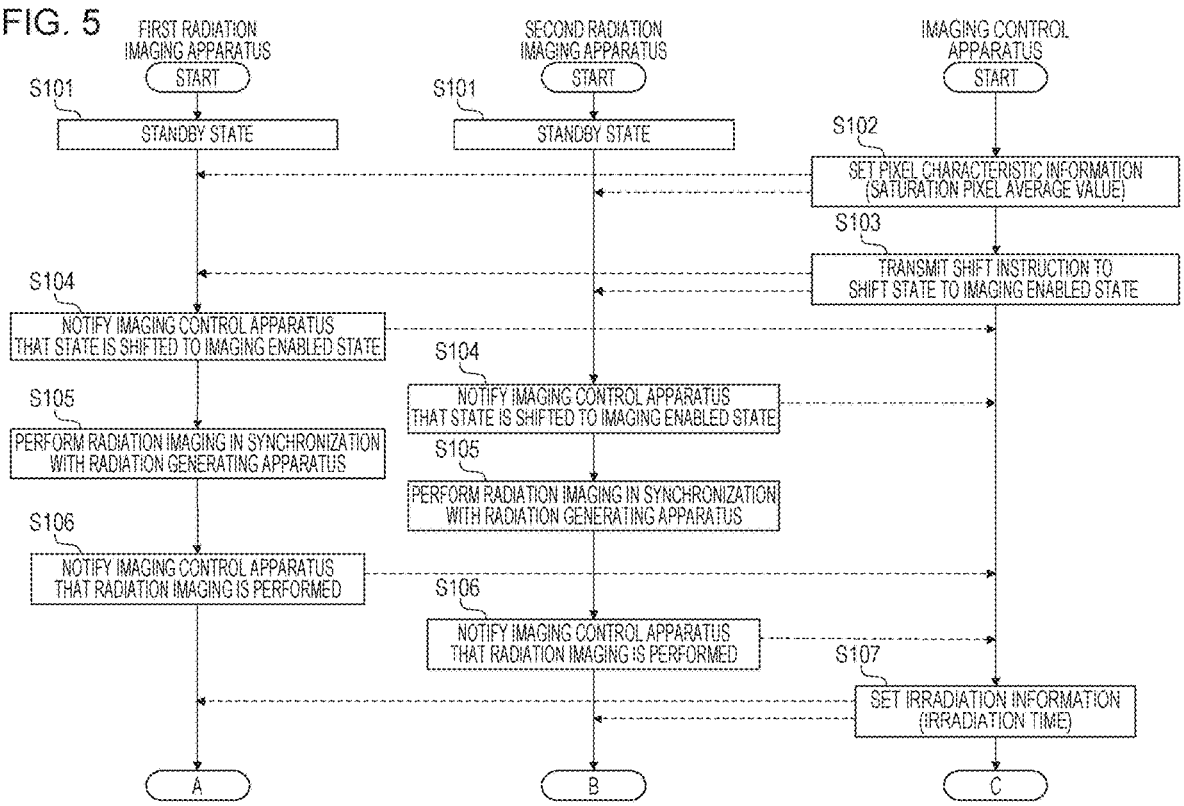
FIG. 5 is a flowchart illustrating an operation of a radiation imaging according to the first embodiment.

FIG. 5 is a flowchart illustrating an example of an operation from preparation of radiation imaging to execution of the radiation imaging by the first radiation imaging apparatus 102 and the second radiation imaging apparatus 103.

At step S101, the first radiation imaging apparatus 102 and the second radiation imaging apparatus 103 are in a standby state. In the standby state, communication is established between the radiation imaging apparatuses and the imaging control apparatus 101.

At step S102, the imaging control apparatus 101 (information setting unit 1012) transmits, to all the available radiation imaging apparatuses, pixel characteristic information that indicates pixel characteristics of the respective pixels of the radiation imaging apparatuses for evaluating pixel values of a radiation image. In the present embodiment, the first radiation imaging apparatus 102 and the second radiation imaging apparatus 103 are the available radiation imaging apparatuses. The first radiation imaging apparatus 102 and the second radiation imaging apparatus 103 store the pixel characteristic information, which is received via the communication unit 1027, in the storage unit 1023 by using the setting unit 1025. Here, it is set that an average value of pixel values of a saturated radiation image (hereinafter, a saturation pixel average value) is used as the pixel characteristic information.

The pixel characteristic information is not limited thereto, and, for example, a maximum value, a median value, a variance value of the pixel values of the saturated radiation image, or a maximum value of pixel values that are calculated from output performance of the radiation detecting unit 1021 can be used. The pixel values can be luminance values or can be concentration values. While the imaging control apparatus 101 sets a saturation pixel average value to each of the first radiation imaging apparatus 102 and the second radiation imaging apparatus 103 as the pixel characteristic information in the present embodiment, it can be configured such that each of the radiation imaging apparatuses stores the saturation pixel average value in advance. The saturation pixel average value described above can be different or common between the radiation imaging apparatuses.

At step S103, the imaging control apparatus 101 (state managing unit 1016) transmits a shift instruction to shift a state to an imaging enabled state to the first radiation imaging apparatus 102 and the second radiation imaging apparatus 103.

At step S104, the first radiation imaging apparatus 102 and the second radiation imaging apparatus 103 are shifted to the imaging enabled state in response to the shift instruction from the imaging control apparatus 101 and notify the imaging control apparatus 101 that the state is shifted to the imaging enabled state.

At step S105, the first radiation imaging apparatus 102 and the second radiation imaging apparatus 103 perform radiation imaging in synchronization with the radiation generating apparatus 104.

At step S106, the first radiation imaging apparatus 102 and the second radiation imaging apparatus 103 notify the imaging control apparatus 101 that radiation imaging is performed in each of the first radiation imaging apparatus 102 and the second radiation imaging apparatus 103.

At step S107, the imaging control apparatus 101 (information setting unit 1012) transmits, to all the radiation imaging apparatuses that notify that imaging is performed, a time (hereinafter, an irradiation time) during which the radiation generating apparatus 104 radiates radiation as irradiation information. In the present embodiment, the first radiation imaging apparatus 102 and the second radiation imaging apparatus 103 are the radiation imaging apparatuses that notify that imaging is performed. The first radiation imaging apparatus 102 and the second radiation imaging apparatus 103 set the irradiation time, which is received via the communication unit 1027, in the storage unit 1023 using the setting unit 1025.

In the present embodiment, it is set that the imaging control apparatus 101 (information setting unit 1012) transmits, to the first radiation imaging apparatus 102 and the second radiation imaging apparatus 103, the time (irradiation time) during which the radiation generating apparatus 104 radiates radiation. However, a step in which the first radiation imaging apparatus 102 and the second radiation imaging apparatus 103 autonomously calculate the time during which the radiation generating apparatus 104 radiates radiation when imaging operation is performed and set the time in the storage unit 1023 can be provided instead of step S107.

The setting unit 1025 can linearly attenuate the saturation pixel average value based on the irradiation time. The attenuation of the saturation pixel average value is not limited to the linear attenuation, and can be, for example, exponential attenuation, logarithmic attenuation, or attenuation in which multiple types of attenuation are combined. This enables performing appropriate determination even for a radiation image that is generated with pixel values saturated due to long time irradiation with radiation.

Figure 6:
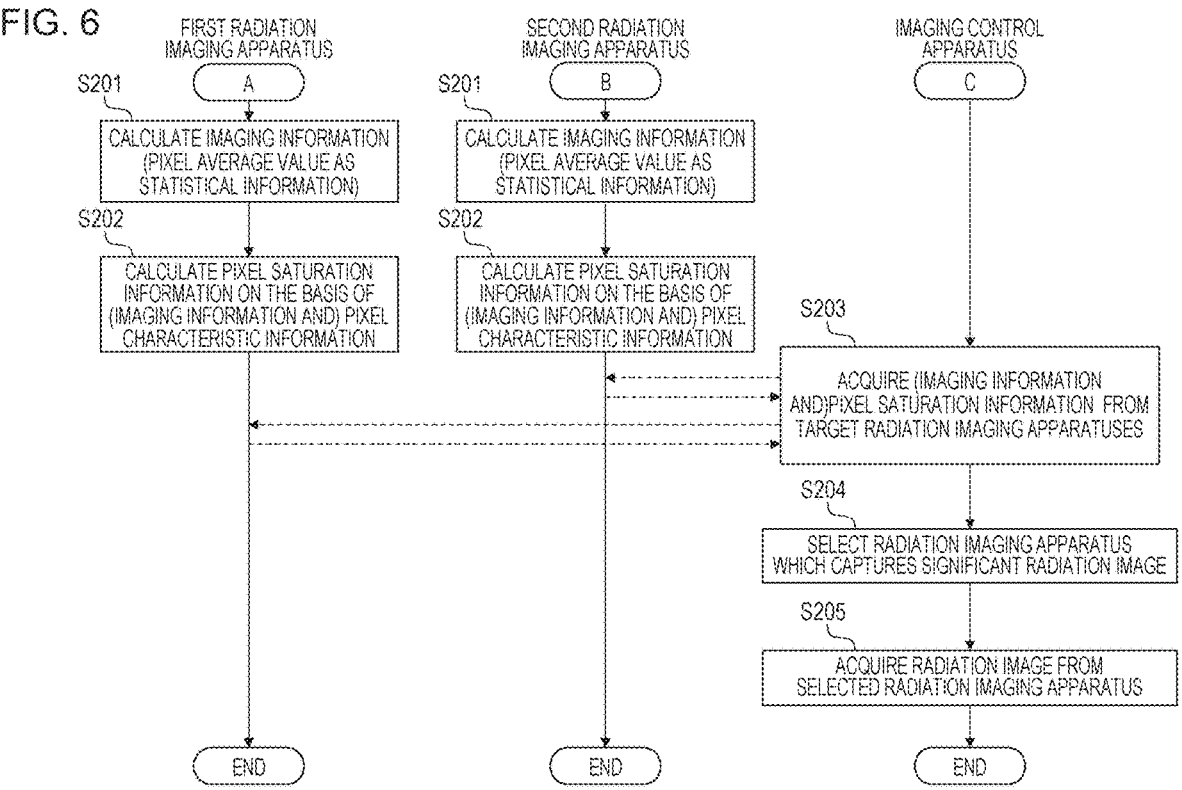
FIG. 6 is a flowchart illustrating an operation of acquiring a radiation image according to the first embodiment.

FIG. 6 is a flowchart illustrating an example of an operation after execution of radiation imaging by the first radiation imaging apparatus 102 and the second radiation imaging apparatus 103 until acquisition of a radiation image by the imaging control apparatus 101.

At step S201, the imaging information generating unit 1024 of the first radiation imaging apparatus 102 and the second radiation imaging apparatus 103 generates statistical information of pixel values of the generated radiation image as the imaging information and sets the statistical information in the storage unit 1023. Here, as an example of the statistical information that is the imaging information, an average value of the pixel values (hereinafter, a pixel average value) of the radiation image is used. The statistical information as the imaging information is not limited thereto, and information that is comparable to the pixel characteristic information can be used. For example, a maximum value, a median value, a variance value of the pixel values of the radiation image, or the like can be used.

Alternatively, statistical information such as a maximum value of difference between pixel values of pixels adjacent to each other or a width between the maximum value and the minimum value of the pixel values, can be used. Additionally, two or more pieces of statistical information can be generated. As an example of the statistical information, a variation (hereinafter, pixel value variation) of pixel values of the radiation image can be used. The pixel value variation of a radiation image can be, for example, a median value, a variance value of the pixel values of the radiation image, a width between a maximum value and a minimum value of the pixel values, a histogram, a statistical distribution function, or the like. The pixel values can be luminance values or concentration values.

At step S202, the calculation unit 1026 of each of the first radiation imaging apparatus 102 and the second radiation imaging apparatus 103 calculates the pixel saturation information from the pixel average value as the imaging information by using the saturation pixel average value as the pixel characteristic information that is stored in the storage unit 1023. Here, the pixel saturation information is information indicating whether a part or all of the pixels of the radiation image are saturated. When the pixel average value is greater than or equal to the saturation pixel average value, the calculation unit 1026 calculates, as the pixel saturation information, information indicating that a part or all of the pixels of the radiation image are saturated (hereinafter, a saturated state). When the pixel average value is less than the saturation pixel average value, the calculation unit 1026 calculates, as the pixel saturation information, information indicating that the pixels of the radiation image are not saturated (hereinafter, a non-saturated state). The communication unit 1028 transmits the calculated pixel saturation information to the imaging control apparatus 101.

At step S203, the imaging control apparatus 101 (information acquiring unit 1013) acquires, from the first radiation imaging apparatus 102 and the second radiation imaging apparatus 103, pixel average values as the imaging information generated at step S201 and the pixel saturation information calculated at step S202.

At step S204, the imaging control apparatus 101 (selecting unit 1014) compares the pixel average values as the imaging information acquired at step S203 while taking the pixel saturation information acquired at step S203 into account. Each of the pixel average values as the imaging information includes a data size smaller than that of the radiation image. Here, when the pixel saturation information of all the radiation imaging apparatuses indicates the non-saturated state, the selecting unit 1014 selects a radiation imaging apparatus that provides a maximum pixel average value.

When the pixel saturation information of one or more radiation imaging apparatuses indicates the saturated state and the pixel saturation information of at least one or more radiation imaging apparatuses indicates the non-saturated state, the selecting unit 1014 selects a radiation imaging apparatus that includes the pixel saturation information indicating the non-saturated state and provides a maximum pixel average value. When the pixel saturation information of all the radiation imaging apparatuses indicates the saturated state, the selecting unit 1014 can select a radiation imaging apparatus that notifies earlier that radiation imaging is performed. In such a manner, by selecting a radiation imaging apparatus based on the pixel saturation information indicating whether a part or all of the pixels of the radiation image are saturated, accuracy in selection of a significant radiation image from a plurality of radiation imaging apparatuses capable of imaging is improved.

At step S205, the imaging control apparatus 101 (image acquiring unit 1015) acquires a radiation image from the radiation imaging apparatus as the first radiation imaging apparatus 102 here) that is selected at step S204. That is, the imaging control apparatus 101 requests an image to the first radiation imaging apparatus 102 and the communication unit 1027 of the first radiation imaging apparatus 102 transmits, to the imaging control apparatus 101, a radiation image in response to the request of the image from the imaging control apparatus 101.

As described above, in a system in which radiation imaging is performed with a plurality of radiation imaging apparatuses in the imaging enabled state, the imaging control apparatus 101 selects, based on first imaging information (for example, pixel average values) and pixel saturation information that are based on a radiation image, a radiation imaging apparatus from which a radiation image is to be acquired. That is, the imaging control apparatus 101 selects a radiation imaging apparatus that captures a radiation image in which pixels are not saturated. Thus, the imaging control apparatus 101 selects a radiation imaging apparatus that captures a significant radiation image compared to a configuration in which a radiation image is acquired by comparing imaging information (for example, pixel average values) based on only radiation images captured from all the radiation imaging apparatuses. Accordingly, a radiation imaging system that acquires a significant radiation image while reducing a possibility of giving ineffective exposure due to re-imaging is realized.

Second Embodiment

A functional configuration of a radiation imaging system of a second embodiment is similar to that of the first embodiment (FIG. 1). An internal structure of an imaging control apparatus in the second embodiment is similar to that of the first embodiment (FIG. 2). The information acquiring unit 1013 in the second embodiment acquires pixel average values and pixel value variations as the imaging information. The selecting unit 1014 in the second embodiment selects one radiation imaging apparatus from among a plurality of radiation imaging apparatuses based on the pixel average values and the pixel value variations as the imaging information. An internal structure of a radiation imaging apparatus of the second embodiment is similar to that of the first embodiment (FIG. 3). The imaging information generating unit 1024 in the second embodiment includes a function of generating, in addition to the first imaging information, a pixel value variation based on a radiation image or a pixel average value that is stored in the storage unit 1023. The communication unit 1027 in the second embodiment includes, in addition to the functions of the first embodiment, a function of transmitting the pixel value variation generated by the imaging information generating unit 1024.

Figure 7:
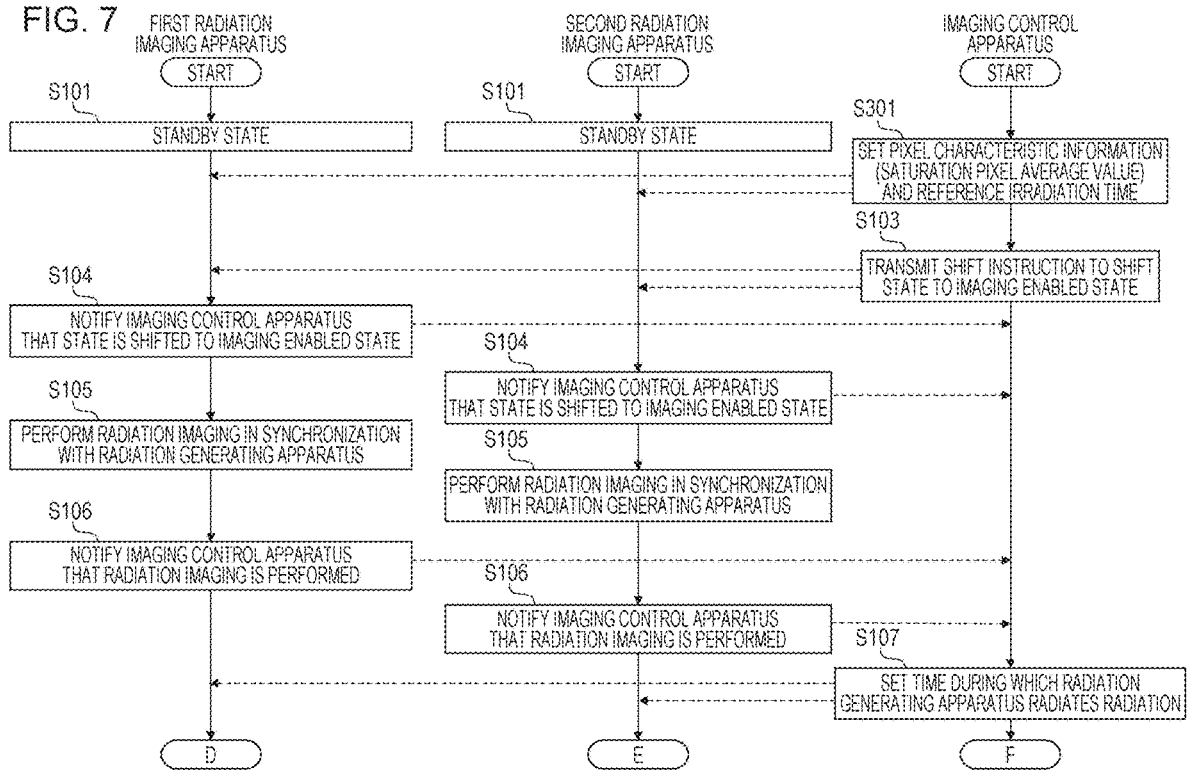
FIG. 7 is a flowchart illustrating an operation of radiation imaging according to a second embodiment.

FIG. 7 is a flowchart illustrating an example of an operation from preparation of radiation imaging to execution of the radiation imaging by the first radiation imaging apparatus 102 and the second radiation imaging apparatus 103 of the second embodiment. The same step number is associated with an operation similar to that of the first embodiment (FIG. 5), and detailed description thereof will be omitted.

At step S301, the imaging control apparatus 101 (information setting unit 1012) transmits, to all available radiation imaging apparatuses, pixel characteristic information and an irradiation time (hereinafter, a reference irradiation time) as a reference. The first radiation imaging apparatus 102 and the second radiation imaging apparatus 103 store the pixel characteristic information and the reference irradiation time that are received via the communication unit 1027 in the storage unit 1023 by using the setting unit 1025. Here, the saturation pixel average value is used as the pixel characteristic information.

Figure 8:
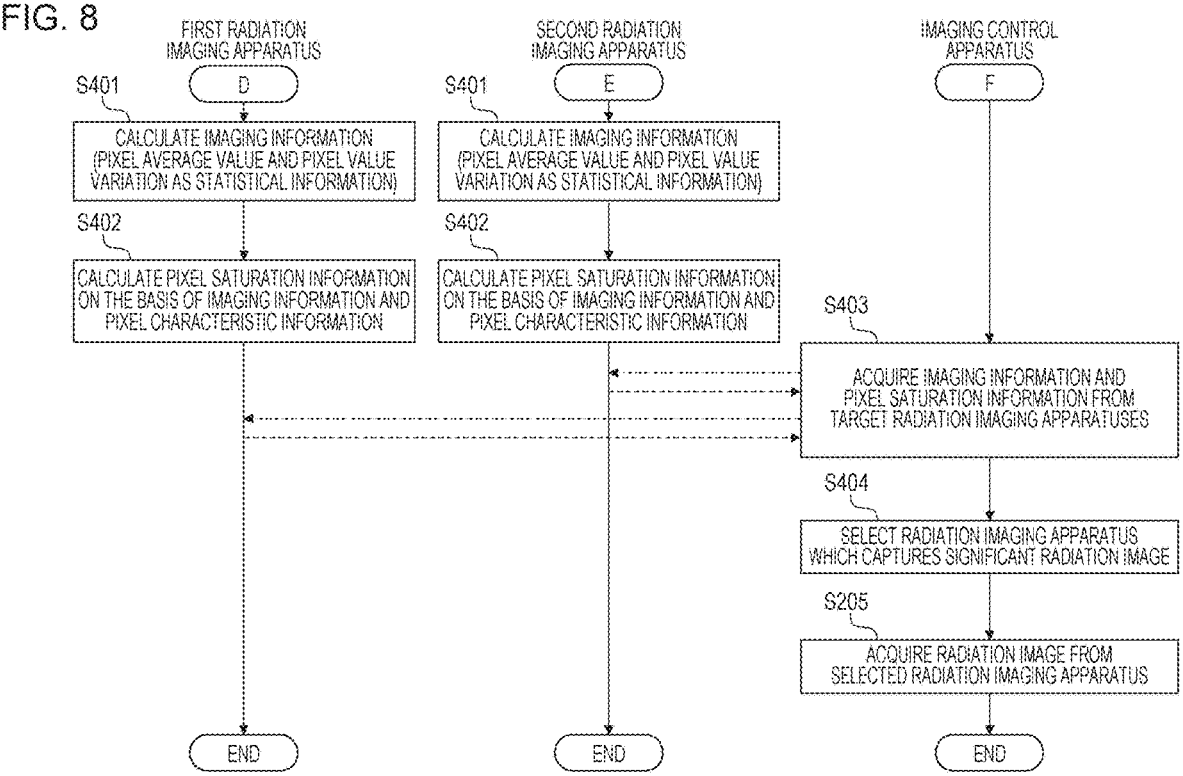
FIG. 8 is a flowchart illustrating an operation of acquiring a radiation image according to the second embodiment.

FIG. 8 is a flowchart illustrating an example of an operation after execution of radiation imaging by the first radiation imaging apparatus 102 and the second radiation imaging apparatus 103 of the second embodiment until acquisition of a radiation image by the imaging control apparatus 101. The same step number is associated with an operation similar to that of the first embodiment (FIG. 6), and detailed description thereof will be omitted.

At step S401, the imaging information generating unit 1024 of the first radiation imaging apparatus 102 and the second radiation imaging apparatus 103 generates statistical information of pixel values of the generated radiation image as the imaging info cation and sets the statistical information in the storage unit 1023. Here, as the imaging information, the pixel average value and the pixel value variation are used.

At step S402, the calculation unit 1026 of the first radiation imaging apparatus 102 and the second radiation imaging apparatus 103 generates pixel saturation information from the pixel average value by using the saturation pixel average value, the pixel value variation, the reference irradiation time, and the irradiation time that are stored in the storage unit 1023. When the pixel average value is greater than or equal to the saturation pixel average value and the irradiation time is shorter than the reference irradiation time, the calculation unit 1026 calculates information indicating that pixels of the radiation image are saturated (hereinafter, a saturated state) as the pixel saturation information. When the pixel average value is less than the saturation pixel average value and the irradiation time is equal to or longer than the reference irradiation time, the calculation unit 1026 calculates information indicating that the pixels of the radiation image are excessively saturated (hereinafter, a supersaturated state) as the pixel saturation information. When the pixel average value is less than the saturation pixel average value and the irradiation time is shorter than the reference irradiation time, the calculation unit 1026 calculates information indicating that the pixels of the radiation image are not saturated (hereinafter, a non-saturated state) as the pixel saturation information. When offset correction in which an offset image acquired from a dark electric charge component without emitting the radiation is subtracted from the radiation image that is saturated due to long time irradiation with radiation, a radiation imaging apparatus at step S404 described below is appropriately determined.

At step S403, the imaging control apparatus 101 (information acquiring unit 1013) acquires the pixel average values and the pixel value variations that are calculated at step S401 and the pixel saturation information calculated at step S402 from the first radiation imaging apparatus 102 and the second radiation imaging apparatus 103. At step S404, the imaging control apparatus 101 (selecting unit 1014) compares pixel average values acquired at step S403 while taking the pixel saturation information and the pixel value variations that are acquired at step S403 into account.

When the pixel saturation information of all of the radiation imaging apparatuses indicates the non-saturated state, the selecting unit 1014 selects a radiation imaging apparatus that provides a maximum pixel average value. Additionally, when the pixel saturation information of at least one or more radiation imaging apparatuses indicates the saturated state and the pixel saturation information of at least one or more radiation imaging apparatuses indicates the non-saturated state, the selecting unit 1014 selects a radiation imaging apparatus with the pixel saturation information indicating the non-saturated state and provides a maximum pixel average value. When the pixel saturation information of at least one or more radiation imaging apparatuses indicates the non-saturated state and the pixel saturation information of at least one or more radiation imaging apparatuses indicates the supersaturated state, the selecting unit 1014 selects a radiation imaging apparatus with the pixel saturation information indicating the non-saturated state and provides a maximum pixel average value.

The selecting unit 1014 can further compare the pixel value variations to select a radiation imaging apparatus that provides a maximum pixel value variation. When the pixel saturation information of all the radiation imaging apparatuses indicates the saturated state, the selecting unit 1014 can select a radiation imaging apparatus that notifies earlier that radiation imaging is performed. When the pixel saturation information of all the radiation imaging apparatuses indicates the supersaturated state, the selecting unit 1014 can select a radiation imaging apparatus that notifies earlier that radiation imaging is performed. When the pixel saturation information of at least one or more radiation imaging apparatuses indicates the saturated state and the pixel saturation information of at least one or more radiation imaging apparatuses indicates the supersaturated state, the selecting unit 1014 can select a radiation imaging apparatus that notifies earlier that radiation imaging is performed.

As described above, according to the second embodiment, a pixel value variation of pixel values is further generated as the imaging information. By using the reference irradiation time, the selecting unit 1014 performs selection by taking the supersaturated state due to long time irradiation with radiation into account. Thus, accuracy in selection of a significant radiation image from a plurality of radiation imaging apparatuses improves. A radiation imaging system that acquires a significant radiation image while reducing a possibility of giving ineffective exposure due to re-imaging is realized.

Third Embodiment

Figure 9:
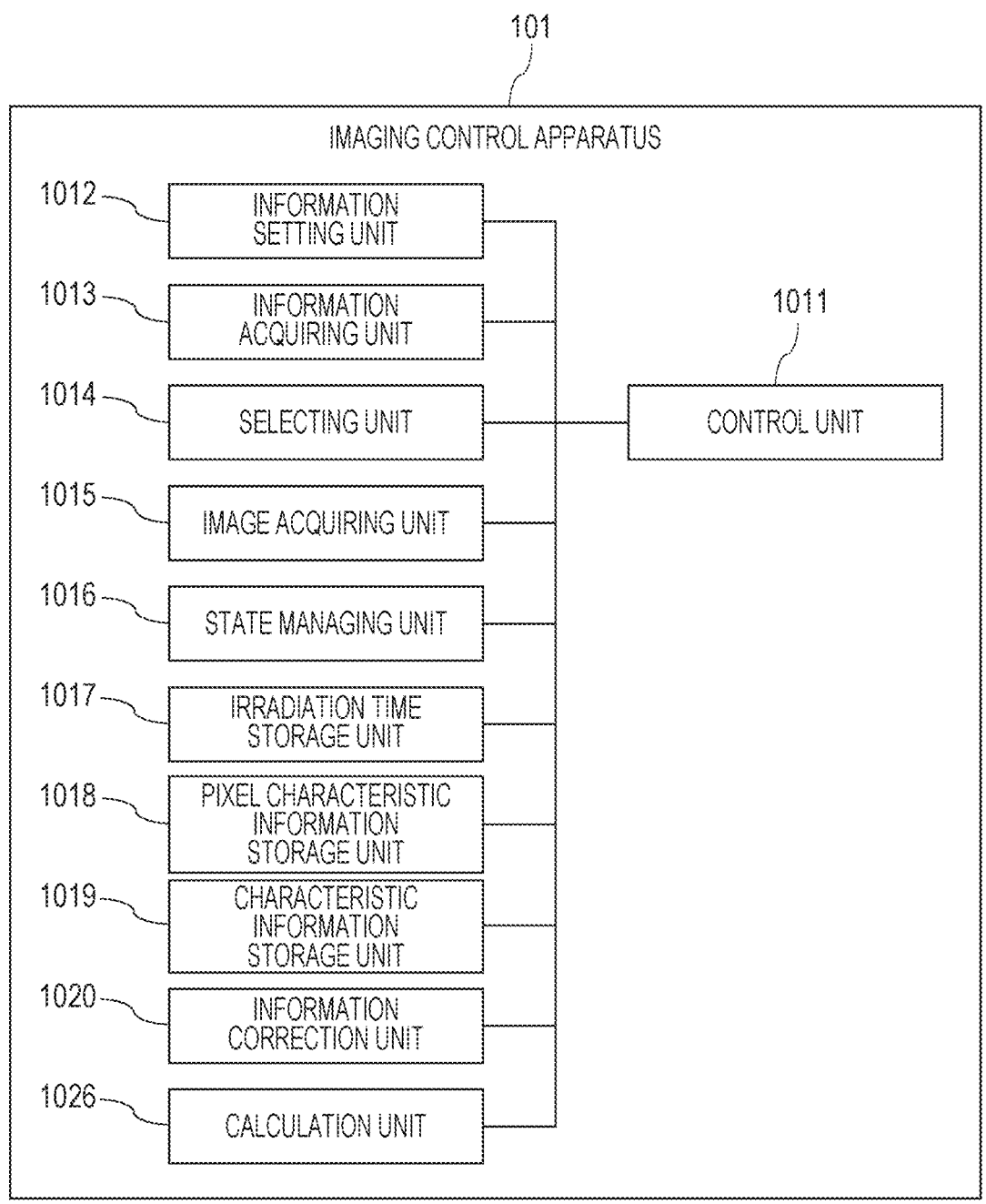
FIG. 9 is a block diagram illustrating a functional configuration of an imaging control apparatus of a third embodiment.

A functional configuration of a radiation imaging system of a third embodiment is similar to that of the first embodiment (FIG. 1). FIG. 9 illustrates an internal structure of an imaging control apparatus in the third embodiment. The same reference number is provided to a configuration similar to that of the first embodiment (FIG. 2). The imaging control apparatus 101 of the third embodiment is configured to include an irradiation time storage unit 1017, a pixel characteristic information storage unit 1018, a characteristic information storage unit 1019, an information correction unit 1020, and the calculation unit 1026 in addition to the configuration of the first embodiment. The information acquiring unit 1013 includes a function of acquiring, from a plurality of radiation imaging apparatuses, pixel characteristic information and apparatus characteristic information of the radiation imaging apparatuses, in addition to a function similar to that of the first embodiment.

The irradiation time storage unit 1017 stores a time during which radiation is radiated and that is acquired from the radiation generating apparatus 104. The pixel characteristic information storage unit 1018 stores the pixel characteristic information of each of the plurality of radiation imaging apparatuses. The characteristic information storage unit 1019 stores the apparatus characteristic information that indicates characteristics of each of the plurality of radiation imaging apparatuses and that is acquired by the information acquiring unit 1012. An example of the apparatus characteristic information includes sensitivity information that indicates a pixel value that is converted when an element that receives radiation in a radiation imaging apparatus receives radiation of 1 mR (milliroentgen). As the sensitivity information, for example, a ratio of a target value of a pixel average value that can be acquired when a radiation imaging apparatus is irradiated with radiation under a predetermined condition and a pixel average value that is actually acquired can be used.

When the radiation imaging apparatus is a radiation imaging apparatus in which a phosphor that converts radiation into light and a photoelectric conversion element that converts the light into an electric charge are used in combination, the target value can be defined based on a kind of the phosphor. An example of kind of the phosphor includes a cesium iodide (CsI) or gadolinium oxysulfide (GOS). Additionally, as the sensitivity information, an image (gain image) that is generated when radiation imaging is performed under a predetermined condition can be used. The sensitivity information can periodically be updated or can be determined in a manufacturing process.

The apparatus characteristic information is not limited to the above-described sensitivity information. For example, effective pixel information or ineffective pixel information (deficient pixel information) can be used as the apparatus characteristic information. Dark image correction information (or a dark image) obtained by performing an imaging operation without emitting radiation to a radiation imaging apparatus can be used as the apparatus characteristic information. Alternatively, the apparatus characteristic information can include, for example, correction information (sensitivity correction information) for correcting the aforementioned characteristic information (e.g., sensitivity information), such as an imaging environment (such as an atmospheric temperature or a temperature of a radiation imaging apparatus itself) of a radiation imaging apparatus or information of deterioration due to time-dependent change. The apparatus characteristic information of a plurality of radiation imaging apparatuses is not limited thereto, and a plurality of pieces of apparatus characteristic information can be used in combination.

The information correction unit 1020 corrects, based on the apparatus characteristic information stored in the apparatus characteristic information storage unit 1019, the imaging information acquired from the plurality of radiation imaging apparatuses by the information acquiring unit 1013 and the pixel characteristic information stored in the pixel characteristic information storage unit 1018. The calculation unit 1026 generates pixel saturation information from the corrected imaging information using the corrected pixel characteristic information. The selecting unit 1014 selects one radiation imaging apparatus from among the plurality of radiation imaging apparatuses (the first radiation imaging apparatus 102 and the second radiation imaging apparatus 103 in the present embodiment) based on the pixel saturation information calculated by the calculation unit 1026 and the irradiation time during which radiation is performed.

Figure 10:
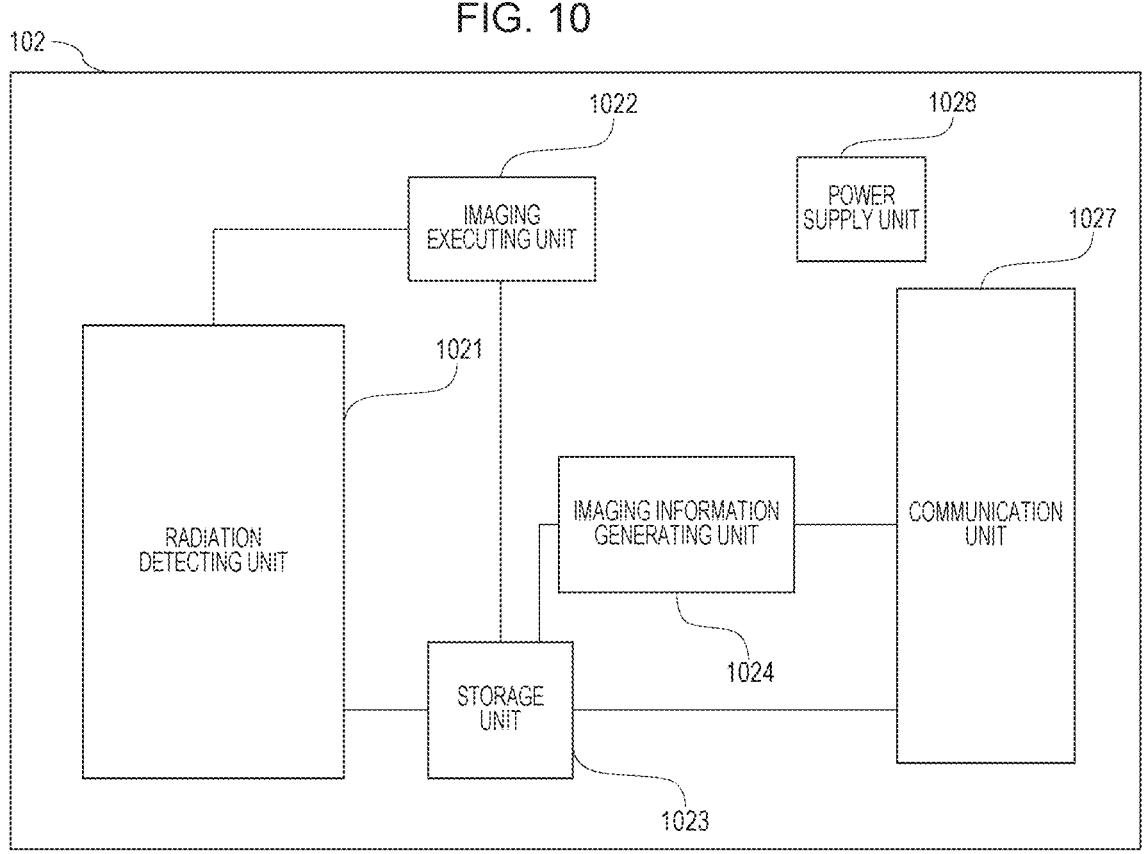
FIG. 10 is a block diagram illustrating an internal structure of a radiation imaging apparatus of the third embodiment.

FIG. 10 illustrates an internal structure of a radiation imaging apparatus in the third embodiment. The same reference number is provided to a configuration similar to that of the first embodiment (FIG. 3). The radiation imaging apparatus of the third embodiment has a configuration in which the setting unit 1025 and the calculation unit 1026 are excluded from the configuration of the first embodiment (FIG. 3).

Figure 11:
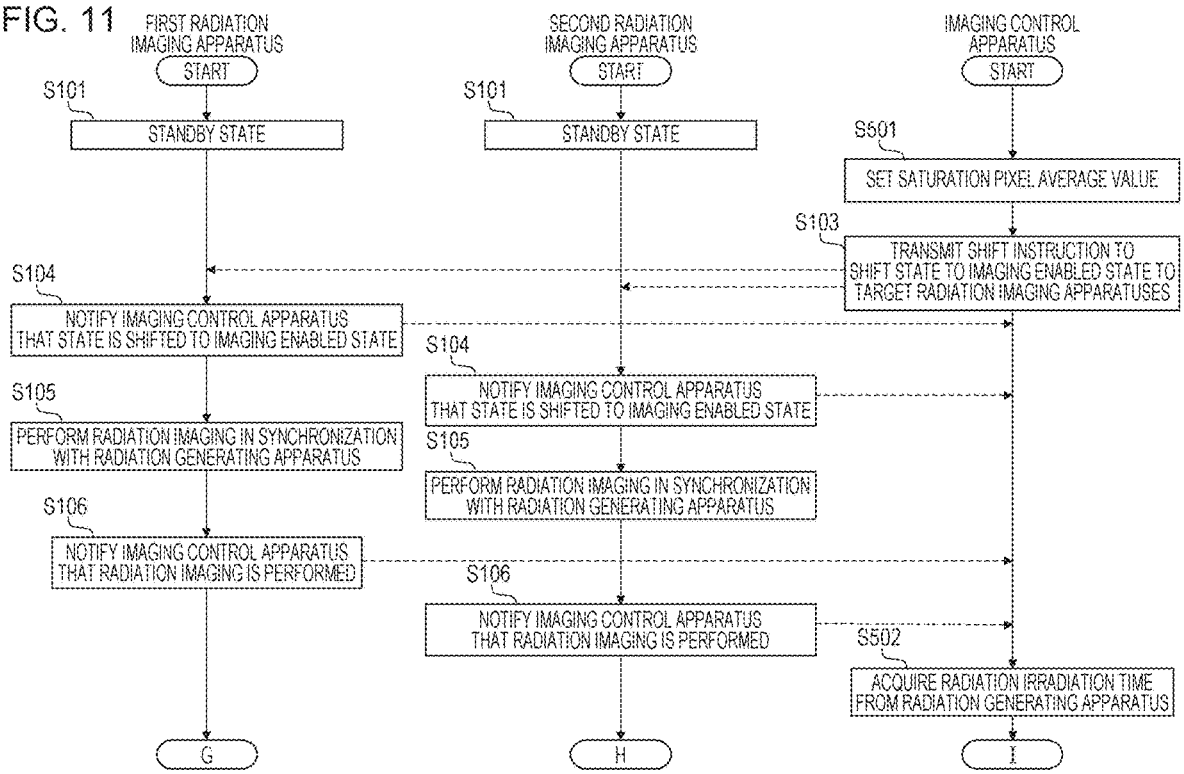
FIG. 11 is a flowchart illustrating an operation of radiation imaging according to the third embodiment.

FIG. 11 is a flowchart illustrating an example of an operation from preparation of radiation imaging to execution of the radiation imaging by the first radiation imaging apparatus 102 and the second radiation imaging apparatus 103 of the third embodiment. The same step number is associated with an operation similar to that of the first embodiment (FIG. 5), and detailed description thereof will be omitted.

At step S501, a saturation pixel average value of each of the plurality of radiation imaging apparatuses, which is acquired by the information acquiring unit 1012 of the imaging control apparatus 101, is stored in the pixel characteristic information unit 1018 as the pixel characteristic information. In the present embodiment, though the saturation pixel average value is provided as an example of the pixel characteristic information, the pixel characteristic information is not limited thereto, and, for example, a maximum value, a minimum value, an average value, a median value, or a variance value of saturated pixel values can be used. Alternatively, a maximum value, a minimum value, an average value, a median value, or a variance value of pixel values that are calculated by output performance of the radiation detecting unit 1021 can be used.

At step S502, an irradiation time of irradiation information of radiation by the radiation generating apparatus 104 that is acquired by the information acquiring unit 1012 of the imaging control apparatus 101 is stored in the irradiation time storage unit 1019.

Figure 12:
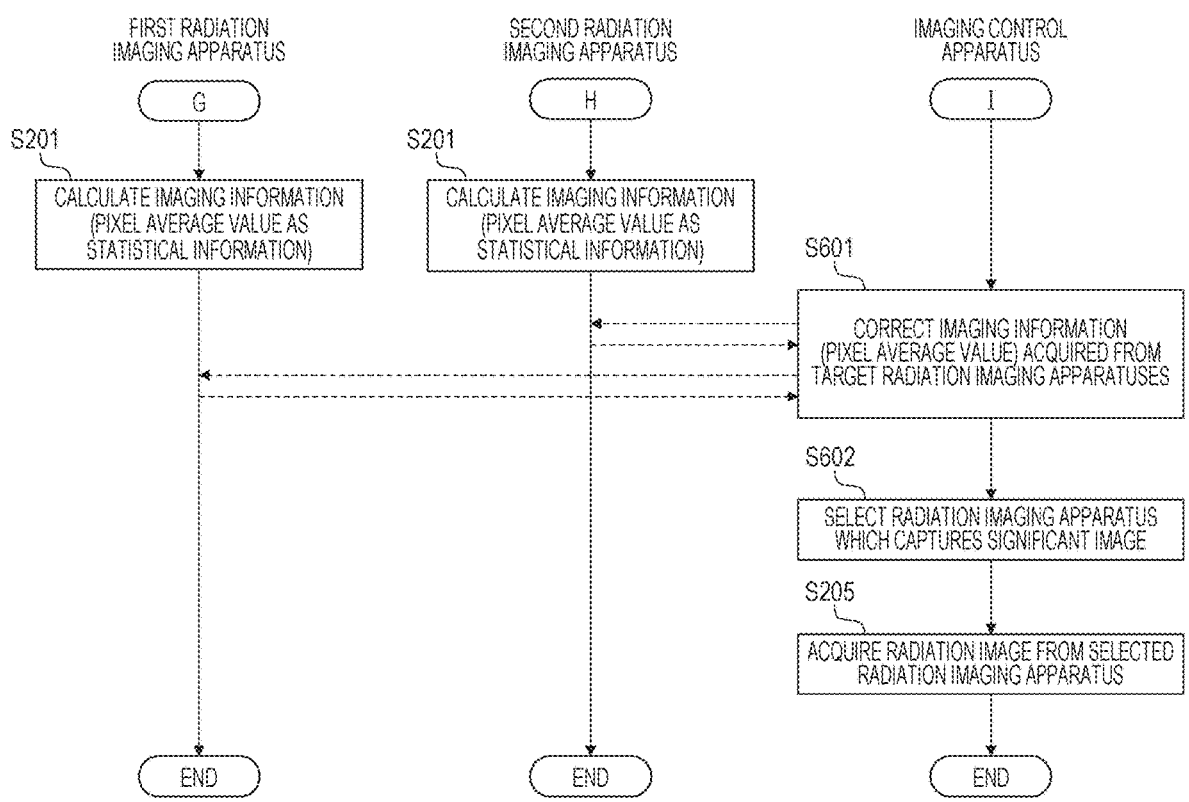
FIG. 12 is a flowchart illustrating an operation of acquiring a radiation image according to the third embodiment.

FIG. 12 is a flowchart illustrating an example of an operation after execution of radiation imaging by the first radiation imaging apparatus 102 and the second radiation imaging apparatus 103 of the third embodiment until acquisition of a radiation image by the imaging control apparatus 101. Step S202 of the first embodiment (FIG. 6) is excluded. The same step number is associated with an operation similar to that of the first embodiment (FIG. 6), and detailed description thereof will be omitted.

At step S601, the imaging control apparatus 101 (information acquiring unit 1013) acquires, from the first radiation imaging apparatus 102 and the second radiation imaging apparatus 103, pixel average values each of which is generated at step S201. The information correction unit 1020 of the imaging control apparatus 101 corrects the pixel average values that are acquired from the plurality of radiation imaging apparatuses and saturation pixel average values that are stored in the pixel characteristic information storage unit 1018, based on the characteristic information stored in the characteristic information storage unit 1019. For example, the information correction unit 1020 uses sensitivity information of the radiation imaging apparatuses to perform correction into pixel average values when sensitivity of the radiation imaging apparatuses matches predetermined reference sensitivity.

A method of correcting the pixel average value is not limited to the aforementioned method. For example, a reference radiation imaging apparatus from among the plurality of radiation imaging apparatuses can be determined so that a pixel average value of another radiation imaging apparatus is corrected based on sensitivity information of the reference radiation imaging apparatus. In addition, characteristic information (e.g., sensitivity information) can be corrected by using correction information (e.g., sensitivity correction information) indicating change of the characteristic information due to a temperature of the radiation imaging apparatus or an atmospheric temperature, and a pixel average value can be corrected by using the corrected characteristic information.

Information of time-dependent change (a function with respect to a time) that is decided in advance for each of the plurality of radiation imaging apparatuses is stored as the correction information and the characteristic information is corrected based on an operation time of each of the radiation imaging apparatuses. Thus, change in the characteristic information due to time-dependent change is taken into consideration.

The pixel average value can be corrected at a ratio of the number of effective pixels to the total number of pixels obtained from effective pixel information and ineffective pixel information. The pixel average value can be corrected by using a pixel average value calculated from dark correction information or a dark image. The method of correcting the pixel average value is not limited to the aforementioned methods and a plurality of correction methods can be used in combination. With processing as described above, the imaging control apparatus 101 does not need to acquire all of radiation images from the radiation imaging apparatuses can select a significant radiation image by imaging information whose data size is smaller than that of the radiation image.

At step S602, the imaging control apparatus 101 (selecting unit 1014) compares the pixel average values corrected at step S601 while taking the saturation pixel average values that are stored in the pixel characteristic information storage unit 1018 and corrected and the irradiation time that is stored in the irradiation time storage unit 1017 into account. Here, a pixel average value of a saturated radiation image (hereinafter, a saturation pixel average value) is used as the pixel characteristic information. The saturation pixel average value can be linearly attenuated based on a radiation irradiation time that is acquired from the radiation generating apparatus 104 by using the information acquiring unit 1013 of the imaging control apparatus 101. The attenuation of the saturation pixel average value is not limited to the linear attenuation, and can be, for example, exponential attenuation, logarithmic attenuation, or attenuation in which multiple types of attenuation are.

As the saturation pixel average value, a saturation pixel average value that is minimum among saturation pixel average values of all the available radiation imaging apparatuses can be used in common. When the pixel average values of all the radiation imaging apparatuses are less than the saturation pixel average value, a radiation imaging apparatus that provides a maximum pixel average value is selected. When the pixel average values of at least one or more radiation imaging apparatuses are less than the saturation pixel average value and the pixel average values of at least one or more radiation imaging apparatuses are greater than or equal to the saturation pixel average value, a radiation imaging apparatus that provides a maximum pixel average value is selected. When the pixel average values of all the radiation imaging apparatuses are greater than or equal to the saturation pixel average value, the selecting unit 1014 can select a radiation imaging apparatus that notifies earlier that radiation imaging is performed.

As described above, according to the third embodiment, in a system in which radiation imaging is performed with a plurality of radiation imaging apparatuses in the imaging enabled state, the imaging information acquired from the plurality of radiation imaging apparatuses is corrected based on the characteristic information of the respective radiation imaging apparatuses. The imaging control apparatus 101 can compare the imaging information of the plurality of radiation imaging apparatuses by referring to the first imaging information that is corrected. Thus, a possibility of acquiring an image from an incorrect radiation imaging apparatus is further reduced.

Fourth Embodiment

A functional configuration of a radiation imaging system of a fourth embodiment is similar to that of the first embodiment (FIG. 1).

An internal structure of an imaging control apparatus in the fourth embodiment is similar to that of the third embodiment (FIG. 9). The information acquiring unit 1013 in the fourth embodiment acquires a pixel average value and a pixel value variation as statistical information of pixel values of a radiation image that is imaging information. The selecting unit 1014 in the fourth embodiment selects one radiation imaging apparatus from among a plurality of radiation imaging apparatuses based on fourth imaging information in addition to the first imaging information and the pixel saturation information.

An internal structure of a radiation imaging apparatus in the fourth embodiment is similar to that of the third embodiment (FIG. 10). The imaging information generating unit 1024 in the fourth embodiment includes a function of generating two or more pieces of statistical information as the imaging information. The communication unit 1027 in the fourth embodiment includes a function of transmitting two or more pieces of statistical information as the imaging information.

An operation from preparation of radiation imaging to execution of the radiation imaging by the first radiation imaging apparatus 102 and the second radiation imaging apparatus 103 of the fourth embodiment is similar to that of the third embodiment (FIG. 11). After step S106, the information acquiring unit 1013 of the imaging control apparatus 101 acquires, from the radiation generating apparatus 104, a time during which radiation is radiated.

Figure 13:
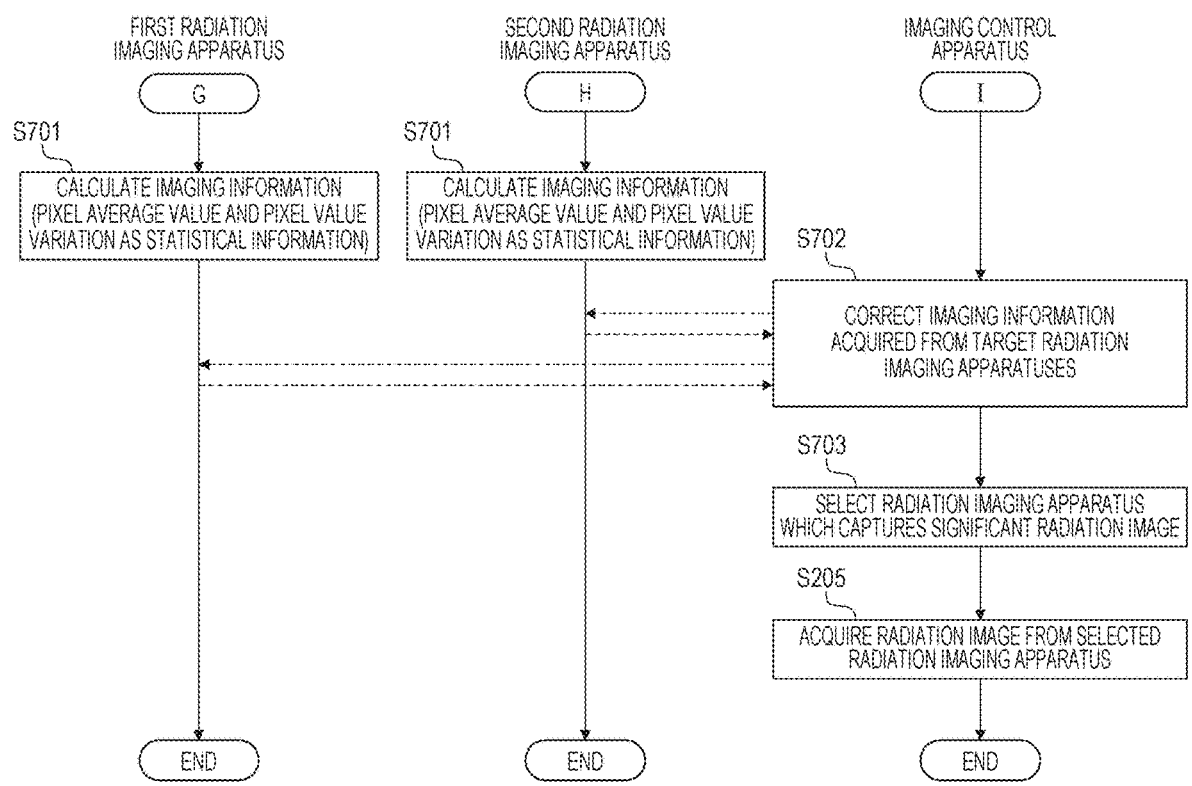
FIG. 13 is a flowchart illustrating an operation of acquiring a radiation image according to a fourth embodiment.

FIG. 13 is a flowchart illustrating an operation after execution of radiation imaging by the first radiation imaging apparatus 102 and the second radiation imaging apparatus 103 of the fourth embodiment until acquisition of a radiation image by the imaging control apparatus 101. The same step number is associated with an operation similar to that of the third embodiment (FIG. 11), and detailed description thereof will be omitted.

At step S701, the imaging information generating unit 1024 of the first radiation imaging apparatus 102 and the second radiation imaging apparatus 103 generates two pieces of statistical information of pixel values of the generated radiation image as the imaging information and sets the two pieces of statistical information in the storage unit 1023. Here, as an example of the two pieces of statistical information, a pixel average value and a pixel value variation are used.

At step S702, the imaging control apparatus 101 (information acquiring unit 1013) acquires, from the first radiation imaging apparatus 102 and the second radiation imaging apparatus 103, pixel average values each of which is calculated at step S701 and pixel value variations each of which is calculated at step S701. The information correction unit 1020 of the imaging control apparatus 101 corrects the pixel average values that are acquired from the plurality of radiation imaging apparatuses and the saturation pixel average values stored in the pixel characteristic information storage unit 1018 based on the characteristic information that is stored in the characteristic information storage unit 1019. The pixel value variation can be corrected. For example, the information correction unit 1020 uses sensitivity information of the radiation imaging apparatuses to perform correction into pixel average values when sensitivity of the radiation imaging apparatuses matches with predetermined reference sensitivity. The method of correcting the pixel average value is not limited to the aforementioned method. For example, a reference radiation imaging apparatus from among the plurality of radiation imaging apparatuses can be decided so that a pixel average value of another radiation imaging apparatus is corrected based on with sensitivity information of the reference radiation imaging apparatus.

Characteristic information (e.g., sensitivity information) can be corrected by using correction information (e.g., sensitivity correction information) indicating change of the characteristic information due to a temperature of the radiation imaging apparatus or an atmospheric temperature, and a pixel average value can be corrected by using the corrected characteristic information. Information of time-dependent change (a function with respect to a time) that is decided in advance for each of the plurality of radiation imaging apparatuses is stored as the correction information and the characteristic information is corrected based on an operation time of each of the radiation imaging apparatuses. Thus, change in the characteristic information due to time-dependent change is taken into consideration.

The pixel average value can be corrected at a ratio of the number of effective pixels to the total number of pixels obtained from effective pixel information and ineffective pixel information. The pixel average value can be corrected by using a pixel average value calculated from dark correction information or a dark image. The method of correcting the pixel average value is not limited to the aforementioned methods and a plurality of correction methods can be used in combination.

At step S703, the imaging control apparatus 101 (selecting unit 1014) compares the pixel average values corrected at step S702 while taking the saturation pixel average values that are stored in the pixel characteristic information storage unit 1018 and corrected and the irradiation time which is stored in the irradiation time storage unit 1017 into account. Here, a saturation pixel average value is used as the pixel characteristic information. The saturation pixel average value can be linearly attenuated based on a radiation irradiation time that is acquired from the radiation generating apparatus 104 by using the information acquiring unit 1013 of the imaging control apparatus 101. The attenuation of the saturation pixel average value is not limited to the linear attenuation, and can be, for example, exponential attenuation, logarithmic attenuation, or attenuation in which multiple types of attenuation are combined.

As the saturation pixel average value, a saturation pixel average value that is minimum among saturation pixel average values of all the available radiation imaging apparatuses can be used in common. When the pixel average value is greater than or equal to the saturation pixel average value and the irradiation time is shorter than a reference value, the pixel saturation information indicating that pixels of a radiation image are saturated (hereinafter, saturated state) is calculated. When the pixel average value is less than the saturation pixel average value and the irradiation time is equal to or longer than the reference value, the pixel saturation information indicating that the pixels of the radiation image are excessively saturated (hereinafter, super-saturated state) is calculated. When the pixel average value is less than the saturation pixel average value and the irradiation time is shorter than the reference value, the pixel saturation information indicating that the pixels of the radiation image are not saturated (non-saturated state) is calculated. The reference value can be stored by the imaging control apparatus 101 in advance based on the radiation imaging apparatus, or can be specified by a user.

When the pixel saturation information of all the radiation imaging apparatuses indicates the non-saturated state, the selecting unit 1014 selects a radiation imaging apparatus that provides a maximum pixel average value. When the pixel saturation information of at least one or more radiation imaging apparatuses indicates the saturated state and the pixel saturation information of at least one or more radiation imaging apparatuses indicates the non-saturated state, the selecting unit 1014 selects a radiation imaging apparatus that includes the pixel saturation information indicating the non-saturated state and provides a maximum pixel average value. When the pixel saturation information of at least one or more radiation imaging apparatuses indicates the non-saturated state and the pixel saturation information of at least one or more radiation imaging apparatuses indicates the supersaturated state, the selecting unit 1014 selects a radiation imaging apparatus that includes the pixel saturation information indicating the non-saturated state and provides a maximum pixel average value. The selecting unit 1014 can further compare the pixel value variations to select a radiation imaging apparatus that provides a maximum pixel value variation.

When pixel saturation information of all the radiation imaging apparatuses indicates the saturated state, the selecting unit 1014 can select a radiation imaging apparatus that notifies earlier that radiation imaging is performed. When the pixel saturation information of all the radiation imaging apparatuses indicates the supersaturated state, the selecting unit 1014 can select a radiation imaging apparatus that notifies earlier that radiation imaging is performed. When the pixel saturation information of at least one or more radiation imaging apparatuses indicates the saturated state and the pixel saturation information of at least one or more radiation imaging apparatuses indicates the supersaturated state, the selecting unit 1014 can select a radiation imaging apparatus that notifies earlier that radiation imaging is performed.

While the above description has been provided based on the exemplary embodiments, the present disclosure is not limited to these specific embodiments and various forms within a range not departed from the scope of the present disclosure is also encompassed.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s)

and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-159759, filed Aug. 22, 2017, which is hereby incorporated by reference herein in its entirety.

What is claimed is:

1. A radiation imaging system comprising:
a plurality of radiation imaging apparatuses each of which includes a radiation detecting unit that performs an imaging operation for capturing a radiation image based on radiation radiated from a radiation generating apparatus, wherein each of the plurality of radiation imaging apparatuses includes a generating unit that generates imaging information whose data size is smaller than that of the radiation image;
a control apparatus that communicates with the plurality of radiation imaging apparatuses;
a calculation unit that calculates information based on the imaging information indicating whether a part or all of pixels of the radiation image are saturated;
a selecting unit that selects one radiation imaging apparatus from among the plurality of radiation imaging apparatuses based on the information; and
an image acquiring unit that acquires a radiation image from the one radiation imaging apparatus selected by the selecting unit.

2. The radiation imaging system according to claim 1, wherein
each of the plurality of radiation imaging apparatuses includes the calculation unit, and
the control apparatus includes the image acquiring unit.

3. The radiation imaging system according to claim 2, wherein
each of the plurality of radiation imaging apparatuses further includes a communication unit that transmits the information.

4. The radiation imaging system according to claim 3, wherein
the generating unit generates statistical information of pixel values of the radiation image as the imaging information,
wherein the statistical information includes one or more of an average value of the pixel values, a maximum value of the pixel values, a median value of the pixel values, a variance value of the pixel values, a maximum value of difference between pixel values of pixels adjacent to each other, or a width between the maximum value and the minimum value of the pixel values.

5. The radiation imaging system according to claim 3, wherein
the generating unit generates statistical information of pixel values of the radiation image as the imaging information,
the generating unit generates a pixel value variation of the radiation image as the statistical information,
wherein the pixel value variation is a variance value of the pixel values, a width between a maximum value of the pixel values and a minimum value of the pixel values, a histogram, or a distribution function.

6. The radiation imaging system according to claim 3, wherein
the control apparatus includes the selecting unit.

7. The radiation imaging system according to claim 6, wherein
the control apparatus includes a storage unit that stores irradiation information of a radiation generating apparatus when the imaging operation is performed, apparatus characteristic information that indicates apparatus characteristics of each of the plurality of radiation imaging apparatuses, and pixel characteristic information that indicates pixel characteristics of each of the plurality of radiation imaging apparatuses and a correction unit that corrects the imaging information based on the apparatus characteristic information, and
the selecting unit selects one radiation imaging apparatus from among the plurality of radiation imaging apparatuses based on the corrected imaging information.

8. The radiation imaging system according to claim 7, wherein the correction unit corrects, based on the apparatus characteristic information, the imaging information of each of the plurality of radiation imaging apparatuses to imaging information when sensitivity of the plurality of radiation imaging apparatuses matches a predetermined reference sensitivity.

9. The radiation imaging system according to claim 8, wherein the reference sensitivity is sensitivity of one radiation imaging apparatus from among the plurality of radiation imaging apparatuses.

10. The radiation imaging system according to claim 7, wherein the pixel characteristic information includes one or more of an average value of pixel values of a saturated radiation image, a maximum value of the pixel values of the saturated radiation image, a median value of the pixel values of the saturated radiation image, or a width between the maximum value and the minimum value of the pixel values of the saturated radiation image.

11. The radiation imaging system according to claim 7, wherein the irradiation information is an irradiation time.

12. The radiation imaging system according to claim 11, further comprising a setting unit that sets the pixel characteristic information,
wherein the setting unit attenuates the pixel characteristic information based on the irradiation time by linear attenuation, exponential attenuation, or logarithmic attenuation.

13. The radiation imaging system according to claim 11, wherein the generating unit generates the information further based on the irradiation time.

14. The radiation imaging system according to claim 1,
wherein each of the plurality of radiation imaging apparatuses further includes a communication unit that transmits the imaging information, and
wherein the control apparatus includes the calculation unit that calculates the information using the imaging information acquired from each of the plurality of radiation imaging apparatuses and the image acquiring unit.

15. The radiation imaging system according to claim 14, wherein the generating unit generates statistical information of pixel values of the radiation image as the imaging information, and the statistical information includes one or more of an average value of the pixel values, a maximum value of the pixel values, a median value of the pixel values, a variance value of the pixel values, a maximum value of difference between pixel values of pixels adjacent to each other, or a width between the maximum value and the minimum value of the pixel values.

16. The radiation imaging system according to claim 14, wherein the generating unit generates statistical information of pixel values of the radiation image as the imaging information, the generating unit generates a pixel value variation of the radiation image as the statistical information, and the pixel value variation is any of a variance value of the pixel values, a width between a maximum value of the pixel values and a minimum value of the pixel values, a histogram, and a distribution function.

* * * * *